United States Patent [19]

Gozes et al.

[11] Patent Number: 5,217,953
[45] Date of Patent: Jun. 8, 1993

[54] VASOACTIVE INTESTINAL PEPTIDE ANTAGONIST

[75] Inventors: Illana Gozes, Ramat Hasharon, Israel; Douglas E. Brenneman, Damascus, Md.; Mati M. Fridkin, Rehovot, Israel; Terry Moody, Monrovia, Md.

[73] Assignee: The United States of America as represented by the Secretary of the Department of Health & Human Services, Washington, D.C.

[21] Appl. No.: 620,410

[22] Filed: Nov. 30, 1990

[51] Int. Cl.⁵ ............... A61K 37/02; C07K 7/10
[52] U.S. Cl. .................. 514/12; 514/2; 530/324; 530/325; 930/170; 930/DIG. 800; 930/DIG. 820; 930/DIG. 821
[58] Field of Search ......... 530/324, 325; 514/12, 514/2; 930/170, DIG. 800, DIG. 820, DIG. 821

[56] References Cited

U.S. PATENT DOCUMENTS 3,879,371  4/1975  Said et al. .................. 530/324
4,939,224  7/1990  Musso et al. ................ 530/324

FOREIGN PATENT DOCUMENTS 0184309  6/1986  European Pat. Off. .
0297068  12/1988  European Pat. Off. .

OTHER PUBLICATIONS

Endo et al, Endocrinol. Japan, vol. 34(6), pp. 927–935, (1987).
Tischler et al, The Journal of Neuroscience, vol. 4 (5), pp. 1398–1404, (May 1984).
Weihe et al, Cell Tissue Res., vol. 236, pp. 527–540, (1984).
Gozes et al, Endocrinology, vol. 125, No. 6, pp. 2945–2949, (Dec. 1989).
Gerdin et al, Biochimica et Biophysica Acta, vol. 757, pp. 366–370, (1983).
Couvineau et al, Biochemical and Biophysical Research Communications, vol. 121, No. 2, pp. 493–498, (1984).
Fournier et al, Peptides, vol. 8, pp. 169–177, (1984).
Robberecht et al, Eur. J. Biochem., vol. 159, pp. 45–49, (1986).
Schaaper et al, Peptides, vol. 8, pp. 167–168. (1984).
Tachibana et al, Peptide Chemistry, T. Shiba & S. Sakakibara (Ed), (1988).
Turner et al, Peptides, vol. 7, pp. 849–854, (1986).
The Merck Manual of Diagnosis and Therapy, 11th Ed. pp. 1368–1371, (1966).

Primary Examiner—Merrell C. Cashion, Jr.
Assistant Examiner—T. D. Wessendorf
Attorney, Agent, or Firm—Townsend and Townsend

[57] ABSTRACT

The present invention relates to a peptide encoding an antagonist of VIP. The invention also relates to a method of using said peptide to antagonize VIP function. The invention further relates to a pharmaceutical composition.

3 Claims, 7 Drawing Sheets

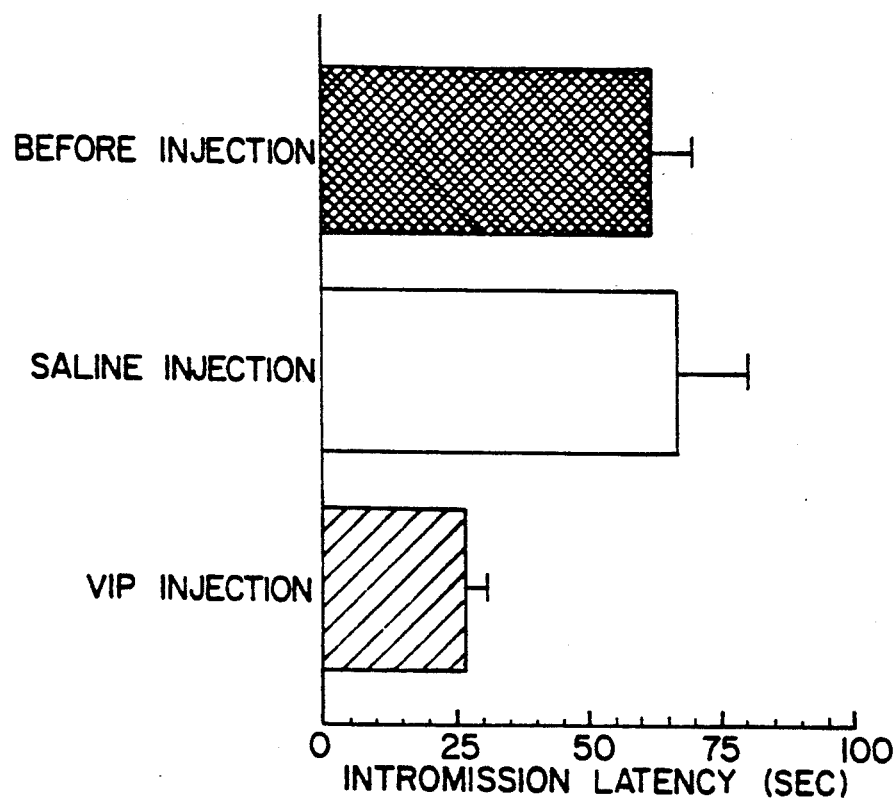
FIG. IA.
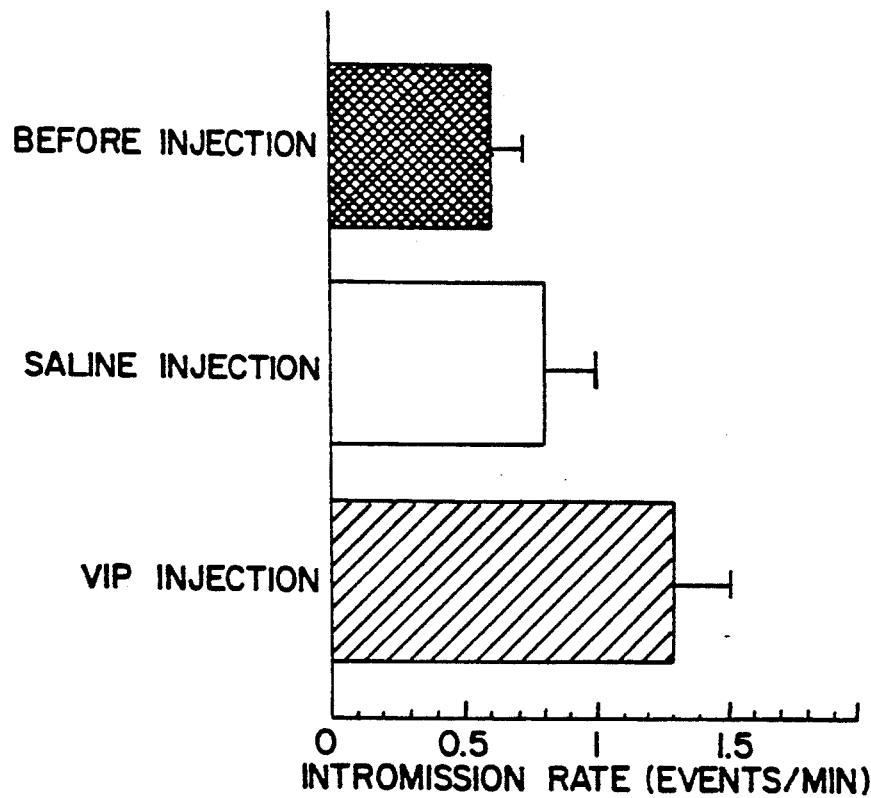
FIG. IB.

VASOACTIVE INTESTINAL PEPTIDE ANTAGONIST

BACKGROUND OF THE INVENTION

1. Field of the Invention

The present invention relates, in general, to a polypeptide. In particular, the present invention relates to an antagonist of vasoactive intestinal peptide.

2. Background Information

Vasoactive intestinal polypeptide (VIP) is a widely distributed peptide hormone which mediates a variety of physiological responses including gastrointestinal secretion, relaxation of gastrointestinal, vascular, and respiratory smooth muscle, lipolysis in adipocytes, pituitary hormone secretion, and excitation and hyperthermia after injection into the central nervous system (Snedecor and Cochran (1967) Statistical Methods pp. 508-509. Ames, Iowa: ISU Press; Said (1981) In: Gut Hormones, Bloom and Polak, eds., Ed. 2, pp. 379-384, New York: Churchhill-Livingston, Inc.). VIP is synthesized as a preprohormone composed of 170 amino acid residues (Cuttitta et al. (1988) J. Clin. Endo. Met. 67:576-583). VIP, a 28 amino acid peptide with an amidated C-terminal, results from posttranslational processing (Said & Mutt (1970) Science 69:1217-1218). The VIP peptide has been shown to contain at least two functional regions, a region involved in receptor specific binding and a region involved in biological activity (Gozes & Brenneman (1989) Molecular Neurobiology 3:201-236).

Another biological function of VIP is as a modulatory agent in the central nervous system (CNS) and periphery (Said & Mutt (1970) Science 69:1217-1218). In the rat brain, VIP elevates cAMP levels and stimulates adenylate cyclase in the cortex, striatum, hypothalmus, hippocampus, thalamus, and midbrain (Deschodt-Lanckman et al. (1977) FEBS Lett. 83:76-80; Etgen and Browning (1983) J. Neurosci. 3:2487-2493; Kerwin et al. (1980) J. Pharm. Pharmacol. 32:561-566; Quick et al. (1978) Biochem. Pharmacol. 27: 2209-2213). Further, VIP fulfills several criteria for a neurotransmitter mediating penile erection. It is present in nerve fibers innervating cavernous smooth muscle and blood vessels and is elevated during erection [Ottesen et al. (1984) Br. Med. J. 288:9; Dixon et al. (1984) J. Endocrinol. 100:249]. Injection of exogenous VIP induces erection in man (Ottesen et al. (1984) Br. Med. J. 288:9) and penile levels have been shown to be decreased in impotent men (Gu et al. (1984) Lancet 2:315). Since VIP appears to be important in erection formation (Anderson et al. (1984) J. Physiol. 350:209), its administration might help in relieving penile dysfunction.

VIP is also biologically active in the mammalian lung and has been found to be colocalized to cholinergic neurons in the lung (Shimosegawa et al. (1989) Reg. Peptides 2:181). Endogenous VIP is present in nerves supplying airway smooth muscle as well as glands and in pulmonary vessels within the normal adult lung (Ley et al. (1981) Cell Tissue Res. 220:238). VIP functions in the lung as a bronchodilator and relaxes pulmonary vascular smooth muscles (Diamond et al. (1983) Am. Rev. Respir. Dis. 128:827-832; Greenburg et al (1985) Thorax 40:715P; Morice et al.(1984) Lancet 1:457-458). Also, VIP is deficit in the airways of patients with bronchial asthma (Lebacq-Verheyden et al. (1988) J. Cell. Biochem. 36:85-96).

The actions caused by VIP may be mediated by specific receptors. VIP receptors were initially detected in the CNS using brain homogenates (Robberecht et al. (1978) Eur. J. Biochem. 90:147-154) and more recently autoradiographic studies have localized the receptors to discrete brain areas such as the cerebral cortex, striatum, supraoptic nucleus of the hypothalmous, dentate gyrus, pinneal and area postrema (Besson et al. (1984) Peptides 5:339-340; DeSouza et al. (1985) Neurosci. Lett. 56: 113-120; Shaffer and Moody (1986) Peptides 7:283-288). VIP receptors have also been characterized in liver membranes (Bataille et al. (1974) Endocrinology 95:713-721) and pancreatic acinar cells (Christophe et al. (1976) J. Biol. Chem. 251:4629-4634).

The biological actions of VIP in the lung may also be mediated by VIP receptors which have been detected in binding assays using plasma membranes derived from the rat, mouse, guinea pig, and human lung (Christophe et al. (1981) Peptides 2:253-258; Dickinson et al. (1986) Peptides 7:791-800; Robberecht et al. (1982) Peptides 4:241-250). Using in vitro autoradiographic techniques and lung slices, VIP receptors have been localized to the alveoli and epithelium of the rat lung and pulmonary artery smooth muscle and alveolar walls of the human lung (Leroux et al. (1984) Endocrinology 114:1506-1512; Leys et al. (1984) FEBS Lett. 199:198-202). The lung VIP receptors were characterized using cross-linking techniques and found to have an apparent molecular weight of 67 Kdaltons (Lebacq-Verheyden et al. (1988) Mol. Cell. Biol. 8:3129-3135). Additionally, it has been demonstrated that VIP positively regulates adenylate cyclase activity in the lung (Oilerenshaw et al. (1989) N. Engl. J. Med 320:1244-1248).

Recently, it was determined that VIP receptors are present in the malignant lung (Shaffer et al. (1987) Peptides 8:1101-1106). Lung cancer is a serious public health problem which kills approximately 150,000 people in the United States annually (Minna, J. D. et al (1985) in: Cancer: principles and practice of oncology (DeVita et al., eds.) pp. 507-599). Traditionally lung cancer is treated with chemo and/or radiation therapy but better survival rates might be possible with the development of new modes of therapy. Lung cancer can be divided into small cell lung cancer (SCLC) which accounts for approximately 25% of the lung cancer cases and non-small cell lung cancer (NSCLC). NSCLC can be further subdivided into adenocarcinoma, large cell carcinoma and squamous cell carcinoma each of which account for approximately 25% of the lung cancer cases. SCLC uses bombesin/gastrin releasing peptide (BN/GRP) as an autocrine growth factor (Cuttitta F. et al., (1985) Nature 316, 823-825). Thus SCLC synthesizes and secretes BN/GRP, and BN or GRP bind to cell surface receptors and stimulate the growth of SCLC. Further, NSCLC synthesizes and secretes transforming growth factor alpha (TGF-alpha), which binds to cell surface epidermal growth factor (EGF) receptors and stimulates NSCLC growth (Imanishi L. et al. (1989) J. NAtl. Cancer Inst. 81, 220-223). In contrast, VIP receptors are present in cells derived from SCLC and the three other major types of lung cancer (all members of NSCLC), large cell carcinoma, squamous cell carcinoma, and adenocarcinoma (Shaffer M. M. et al. (1987) Peptides 8, 1101-1106).

The present invention provides a novel VIP antagonist and methods of using same to alter the function of the vasoactive intestinal peptide. The invention further provides a method of inhibiting lung cancer using this antagonist.

SUMMARY OF THE INVENTION

It is a general object of this invention to provide an antagonist for VIP function.

It is a specific object of this invention to provide a polypeptide that serves as an antagonist for VIP function.

It is a further object of the invention to provide a method of antagonizing VIP function.

It is another object of the invention to provide a pharmaceutical composition suitable for use as an antagonist for VIP function.

It is a further object of the invention to provide a method of inhibiting the growth of lung cancer cells.

Further objects and advantages of the present invention will be clear from the description that follows.

In one embodiment, the present invention relates to a peptide that encodes a VIP antagonist comprising an amino acid sequence necessary for VIP receptor binding and an N-terminal amino acid sequence comprising at least 3 basic amino acids.

In another embodiment, the present invention relates to a method of using a peptide to antagonize VIP, wherein said peptide comprises an amino acid sequence necessary for VIP receptor binding and an N-terminal amino acid sequence comprising at least 3 basic amino acids.

In a further embodiment, the present invention relates to a pharmaceutical composition comprising a VIP-antagonizing peptide in an amount effective for inhibiting the growth of lung cancer cells, and a pharmaceutically acceptable diluent, carrier, or excipient.

In yet another embodiment, the present invention relates to a method of inhibiting the growth of lung cancer cells comprising the use of a VIP-antagonizing peptide.

BRIEF DESCRIPTION OF THE DRAWINGS

FIG. 1. VIP stimulated sexual activity in pituitary-transplanted rats. Pituitary-transplanted male rats were injected with 5 $\mu$g VIP, iv. As controls, saline was injected iv at identical volumes. Eight animals were tested for each variable. The mean intromission latency to the first ejaculation or end of the test period (15 min) is depicted for all animals in FIG. 1(A). As the mounts without intromissions represented only a minor fraction (10–20%) of the copulatory events, they were grouped together with the intromissions. Thus, the data presented show the mean interval between copulatory events. An analysis of variance with a Student-Keols multiple comparison of means test indicated that there was a significant difference in intromission latency (interval between copulatory events) after VIP injections ($P<0.01$). FIG. 1(B) The rate of intromissions (copulatory events) per group measured over a 15-min test period. An analysis of variance indicated a significant increase in the VIP-injected animals ($P<0.02$; $n=8$). All results are the mean$\pm$REM.

FIG. 2. VIP-stimulated sexual activity in castrated rats: inhibition by specific antagonists. Rats were castrated and injected with testosterone daily for 14 consecutive days. VIP (5 $\mu$g/animal) and the antagonist (30 $\mu$g/animal) were injected ip in a volume of 0.25 ml.

FIG. 3. PHI inhibits VIP-stimulated sexual behavior. Castrated rats (as in FIG. 2) were tested. Injections were 0.25 ml saline iv. Five micrograms of each peptide were injected per animal. Nine animals were tested for each peptide; at least 24 hr elapsed between tests on the same animal.

FIG. 7. Binding as a function of VIP concentration.

DETAILED DESCRIPTION OF THE INVENTION

Figure 2A:
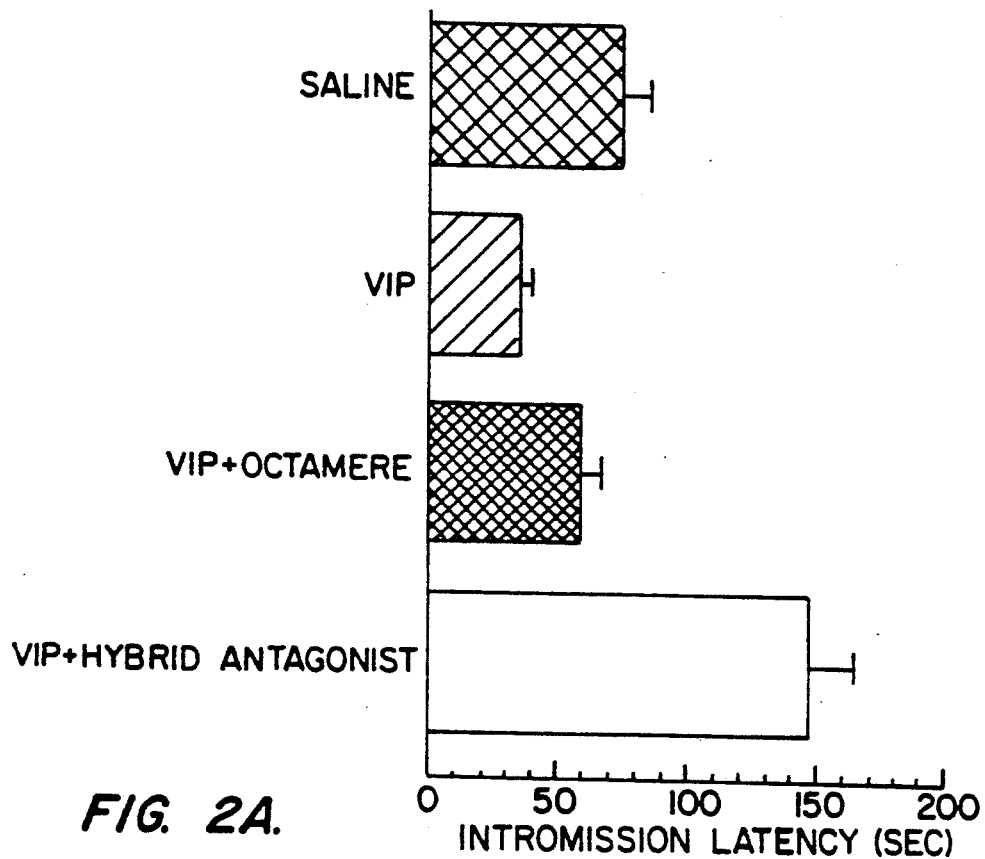
FIG. 2(A) The mean intromission latency interval between copulatory events is shown for saline injection (controls), VIP injection, VIP plus octamere injection, and VIP plus VIP-hybrid antagonist injection. Nine animals were tested for each variable. An analysis of variance indicated a significant decrease in the mean intromission latency after VIP injection, which could be prevented by both antagonists used ($P<0.005$).

The present invention relates to a peptide that encodes a VIP antagonist. The peptide includes an amino acid sequence necessary for VIP receptor binding and an N-terminal amino acid sequence corresponding to a portion of neurotensin in that it includes at least 3 basic amino acids. VIP is a potent vasodilator (Said & Mutt (eds.) 1988 Vasoactive intestinal peptide and related peptides. Ann N.Y. Acad. Sci. 527:1) and neurotensin causes contraction of smooth muscle cells (Carraway & Leeman (1970) Structural requirements for biological activity of neurotensin, a new vasoactive peptide. In: Walter & Meienhofer (eds.) Peptides: Chemistry, Structure and Biology. Ann Arbor Science Publ., Ann Arbor p. 679). Moreover, VIP produces significant increases in cAMP levels in a variety of tissues (Said (ed.) 1982 Vasoactive Intestinal peptide Advances. In: peptide hormone series. Raven Press, New York; Magiatretti & Schorderet (1984) Nature 308:280; Carmena & Prieto (1983) Biochem. Biophya. Acta 763:414). In contrast, neurotensin inhibits cAMP formation through an interaction of the peptide's receptor with the regulatory GTP-binding protein, $N_1$ (Bozou et al. (1986) Mol. Pharmacol. 29:489). This peptide of the present invention was designed to retain the binding properties of VIP for its receptor (for example, amino acids 7-28), but to lack the amino acid sequence necessary for the biological activity, which probably requires the phenylalanine in position 6 (shared by the members of the VIP peptide family (Gozes et al. (1989) Abstract: Society for Neuroscience, Phoenix, Ariz.; Gozes et al. (1989) Endocrinology 125, 2945-2949; Gozes and Brenneman (1989) Molecular Neurobiology 3, 201-236).

Advantageously, the N-terminal amino acid sequence includes the sequence: Lys-Pro-Arg-Arg-Pro-Tyr (SEQ ID No: 1). The concept that a tetrapeptide with basic amino acids at both ends and a proline residue adjacent to the N-terminal amino acid is essential for high activity on membrane permeability has proven correct for neurotensin and other peptides as well (Gerdin et al. (1983) Biochem. Biophys. Acta 757:366-370).

In a preferred embodiment, the peptide antagonist comprises the following amino acid sequence: Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn-$NH_2$ (SEQ ID No: 2).

In another embodiment, the present invention relates to a method of using the above described peptide to antagonize VIP. Broadly, the method comprises administering the peptide antagonist to a mammal in an amount sufficient to antagonize VIP associated functions. In one preferred embodiment, the invention relates to a method of antagonizing VIP function and thereby altering sexual behavior. In a further preferred embodiment, the invention relates to a method of antagonizing VIP function and thereby inhibiting growth of VIP receptor bearing tumor cells, for example, lung tumor cells (for example, NSCLC cells). One skilled in the art will appreciate that the amounts to be administered for any particular treatment protocol can readily be determined. Suitable amounts might be expected to fall within the range of a 1 to 10 mg dose given intranasally three times a day.

In another embodiment, the present invention relates to a pharmaceutical composition comprising the above described VIP-antagonizing peptide in an amount sufficient to inhibit VIP associated activity, and a pharmaceutically acceptable diluent, carrier, or excipient. The pharmaceutical composition of the invention includes the VIP antagonist in a quantity selected depending on the route of administration; intranasally, i.v. or i.p. injection being preferred. Appropriate concentrations and dosage unit sizes can be readily determined by one skilled in the art.

The invention is described in further detail in the following non-limiting examples.

EXAMPLE 1

Synthesis of VIP

Peptides were synthesized using the solid-phase strategy, as described by Barany and Merrifield (1980) In: The Peptides (Gross and Meienhofer Eds.) 2, 1-284, employing manual as well as automatic (applied biosystems 430A peptide synthesizer) procedures.

Assembly of peptide chains proceeds from the carboxyl terminus, attached to the polymeric support, to the amino terminus. Peptides were synthesized on a commercial polystyrene derived support, i.e. possessing p-methylbenzhydryl amine functions. The carboxyl-terminal amino acid derivative is attached to the polymer via dicyclohexylcarbodiimide (DCC)-mediated coupling followed by acetylation of non-reacted amine site on the polymer by acetic anhydride and triethyl amine. Loading of polymers with the amino acid is evaluated by automatic amino acid analyzer following acidic hydrolysis. Substitution levels for synthesis are preferably between 0.25-0.5 mmol amino acid/g polymer. A typical synthesis is performed on a scale of 0.5-1.5 mmol and is initiated with 2-3 g amino acid-derivatized resin. Coupling of amino acids was usually carried out for 45 minutes with performed 1-hydroxy-benzotriazole active ester and with about 3-fold excess of reagents with respect to the available free alpha-amino terminal sites.

The t-butyloxycarbonyl (BOC) group was used for protection of alpha-amino functions throughout synthesis, however, other protecting groups known to the art of amino protection, and are compatible with solid-phase synthesis can be employed.

Side-chain functional moieties employed are as follows: arginine with p-toluene sulfonyl; lysine, 2-chlorobenzyl carbonyl; tyrosine, 2,6-dichlorobenzyl; aspartic acid, serine and threonine, benzyl.

After peptide chain assembly, the amino terminal BOC-group is removed, the polymer is washed with anhydrous ethyl ether and dried in vacuum over $P_2O_5$. The peptide is deprotected and cleaved from the polymeric support by treatment with HF-/p-cresol-p-thiocresol for 1 hour at 0 degrees centigrade. Following removal of HF, the crude peptide-polymer mixture is washed with dry, peroxide free, ethyl ether, extracted with 50% acetic acid in water and then lyophilized.

The resulting preparations were purified by initial passage through a Sephadex G-25 column, while eluting with 1N aqueous acetic acid, followed by preparative high performance liquid chromatography (HPLC) on a Merck Lichrosorb RP-8 (7 $\mu m$; 240×10 mm) employing a linear gradient of acetonitrile (10-80%) in 0.1% aqueous trifluoroacetic acid at a rate of 5 ml/min. Peptide fractions were monitored by UV absorbance at 220 and/or 280 nm. In all cases fractions were collected at peak detection. Purified fractions were analyzed in analytical HPLC (Merck Lichrospher 100 Rp-8, 125×4 mm) using the above gradient.

Peptide correct composition and sequence were ascertained by automated amino acid and sequence analysis, a sample of peptide was hydrolyzed in GN HCl, under vacuum, at 110 degrees centigrade. The sequence of the peptide was determined by Gas Phase ABI 470A protein microsequencer coupled to ABI 120A PTH Analyzer.

EXAMPLE 2

Effects of VIP Antagonist on Sexual Behavior

Male rats were sexually experienced Wistar-derived animals (250–300 g), approximately 3 months old from the Department of Hormone Research, Weizmann Institute of Science. All rats were kept in a 12-hr light, 12-hr dark cycle. Experiments were always conducted within the dark period 2–6 hrs after the onset of darkness. Before testing, each male was put in a separate cage for a period of at least 1 hr. A sexually receptive female (as tested by vaginal smearing) was introduced to each male. Latencies were defined as the intervals between copulatory behaviors (mounts and intromissions). These were recorded over a 15-min period. The latencies to the first copulatory event are reported separately.

The first model of sexually inhibited rats was pituitary-grafted gonadally intact males (Perryman & Thorner (1981) J. Androl 2:233). This procedure results in hyperprolactinemia and a decrease in sexual potency in male rats. Pituitary-transplanted male rats (8 weeks after transplantation) were injected with 5 $\mu$g VIP, iv. As a control, saline iv was injected at identical volumes. The peptide was injected into the tail vein, restraining the animal by hand (two people were involved in the actual injection). The animals were subjected to the behavioral tests immediately after the injection. At least 24 hr elapsed between two consecutive tests per animal (i.e. between saline injection and VIP injection). The doses of VIP were deduced from those used to induce penile erection in men (Ottesen et al. (1984) Br. Med. J. 288:9). The statistical analysis involved a single test measurement per animal.

The second model of sexually inhibited rats was castrated rats. After castration, the animals lose sexual activity in a time-dependent manner (Bradshaw et al. (1981) Endocrinology 109:1047; Reach et al. (1946) J. Exp. Zool. 101:91), and eventually all sexual activities are blocked. Rats were castrated and injected with testosterone (4 $\mu$g/100 g BW) daily for 14 consecutive days. VIP (5 $\mu$g/animal) and the antagonists (30 $\mu$g/animal) were injected ip in a volume of 0.25 ml. Initial experiments were conducted using iv injections; however, as no significant differences were observed between iv and ip administration, ip injections were chosen in this model. When comparisons were made, the same group of rats was injected with one peptide and, after a period of at least 24 hr, with another peptide. The other parameters used for the experiment are described above.

Rat cortical astrocyte cultures were prepared by previously described methods (Evans et al. (1984) J. Neurochem. 43:131; Brenneman et al.(1987) J. Cell Biol. 104:1603). VIP binding studies were conducted on intact cells at 4° C., using PBS containing 0.1% BSA. The cultures (1 mg protein/35 mm culture dish) were incubated with either VIP or the antagonist (10 $\mu$M to 1 pM) for 30 min before the addition of 60 pM [$^{125}$I]VIP at Tyr-22 (2000 Ci/mmol; Amersham Corp., Arlington Heights, Ill). Labeled VIP was incubated with the cultures for 1 hr; the medium was then removed, and cells were washed three times by the addition and rapid removal of 1 ml PBS (at 4° C.). The labeled cells were dissolved in 0.02N NaOH and transferred for radioactivity counting.

The first model of sexually inhibited rats involved pituitary-grafted gonadally intact males (Doherty et al. (1986) Neuroendocrinology 42:358). Sexual behavior was monitored after iv injection of 5 ug VIP in saline. For controls, the same rats were used before injection and after sterile saline injection at identical volumes. A significant reduction in the mean interval between copulatory events coupled to a significant increase in the rate of copulation was observed after the administration of VIP (FIG. 1). A 2- to 3-fold decrease in the latency to the first intromission was observed after VIP injection. Thus, the mean latency to the first mount and intromission was 76$\pm$27 sec in control animals, 76$\pm$30 sec after saline injection, and 23$\pm$4 sec after VIP injection. The latter was significantly decreased compared to that in the saline-injected controls. While only 10–20% of the rats tested ejaculated before VIP treatment, all of the rats ejaculated after administration of the peptide, which is highly significant for VIP. A similar effect was seen in an additional independent experiment which included eight animals.

The second paradigm was the castrated rat model. When animals were tested 14 days after castration, the ip administration of 5 $\mu$g VIP resulted in a 2- to 4-fold drop in the intervals between copulatory events (including the latency to the first intromission); thus, the intromission latency dropped from 90$\pm$16 to 35$\pm$2.4 sec in the six animals tested.

Figure 2B:
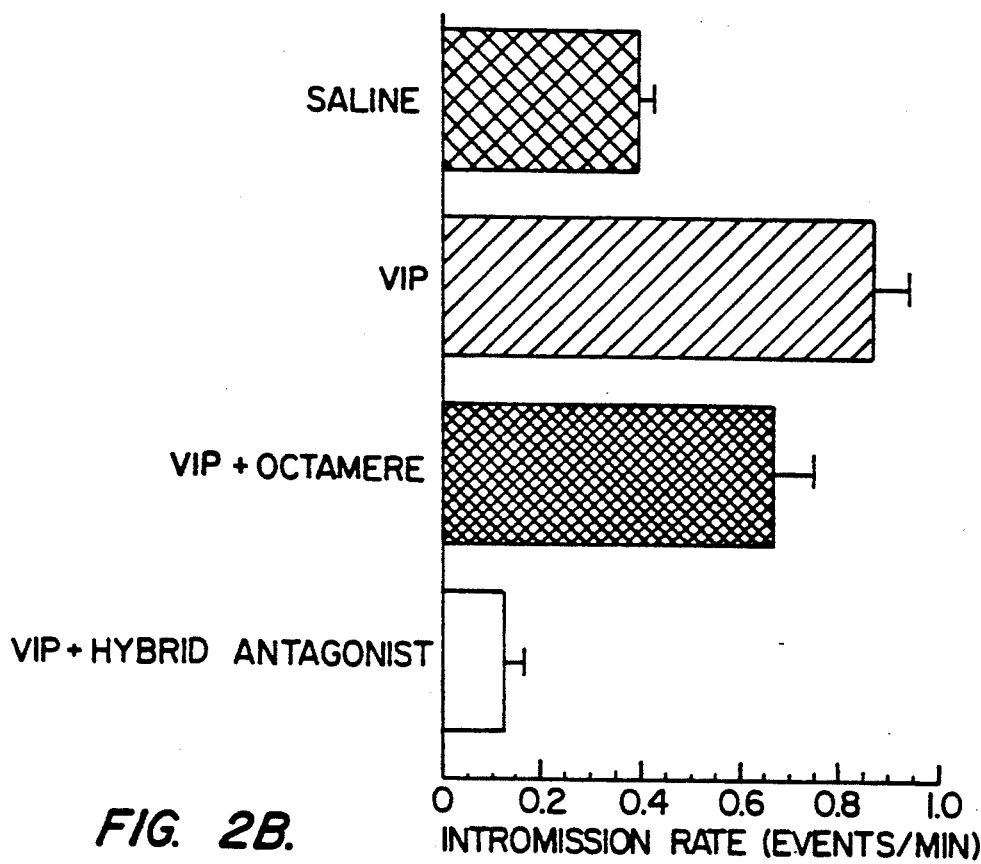
FIG. 2(B) The rate of intromissions (copulatory events) is depicted. The mean values for nine animals per group tested over a 15-min period are shown. A significant increase was observed after VIP injection, which could be prevented by the VIP-hybrid antagonist ($P<0.001$).

Another model was one in which the decrease in sexual behavior after castration was partially reversed by the daily injection of testosterone (4 $\mu$g/100 g BW as indicated). About a 2-fold increase in the rate of intromissions before ejaculation or the end of test period was observed after ip VIP injection compared to that after saline injection (FIG. 2). Thus, VIP increased the number of intromissions per a given test period and induced ejaculations. This was coupled to a 2-fold decrease in intervals (intromission latencies) between copulatory events after VIP injection. The latency to the first intromission decreased from 74$\pm$10 to 40$\pm$9 sec in nine animals tested (P<0.05). Similar results were obtained with iv VIP injection in a group of 6 additional animals. Using this model, it was found that 80–100% of the animals ejaculated after VIP treatment (15 animals were tested in this paradigm). In contrast, when the model without testosterone supplementation was used, only 1 of 6 animals tested ejaculated after VIP treatment. All subsequent experiments were conducted using the castrated rat model supplemented with testosterone. To further demonstrate the specificity of the VIP effects, a VIP receptor binding inhibitor was used, an octamere of the following sequence: Leu-Met-Tyr-Pro-Thr-Tyr-Leu-Lys (SEQ ID NO: 3) (Peninsula, Belmont, Calif.) (Said and Mutt (1988) Ann. N.Y. Acad Sci. 527:1). Simultaneous injection of VIP in the presence of excess (20-fold when expressed as molar ratio) of the octamere specifically inhibited VIP effects on sexual behavior (FIG. 2).

Additional VIP analogs were then designed and synthesized. One analog, the VIP-neurotensin hybrid antagonist, blocked sexual activity after ip injection. Coinjection of this analog with VIP at a 3-fold molar excess of the former resulted in a complete blockade of VIP activity, with values 2-fold lower than the control values (FIG. 2). This was also reflected in the latency to the first copulatory event, which was 92$\pm$20 sec compared to 40$\pm$9 sec with VIP injection by itself. Thus, the VIP-neurotensin hybrid antagonist may serve as a novel VIP antagonist (FIG. 2). As expected, neurotensin by itself inhibited rat sexual behavior, decreasing the number of copulatory events per test period by 2-fold and increasing the intervals by 2-fold (P<0.01 events/min, which is significant according to Student's 1 test).

The VIP-neurotensin hybrid antagonist when injected by itself decreased the rate of copulatory events from 1.66±0.12 to 1.16±0.11 and increased the intromission interval from 36.9±2.4 to 53.4±8.6 sec, in 10 animals (P<0.01). When injected with VIP, the VIP-neurotensin hybrid antagonist decreased activity to below basal levels. One explanation is that the antagonist blocked endogenous VIP, which may contribute to basal sexual activity. As the octamere antagonist had much less of an effect, the results suggest that the VIP-neurotensin hybrid antagonist is more potent. Together, the data above indicate that both neurotensin and VIP can contribute to sexual activity and that the inhibition produced by the antagonist may be only partially due to blockade of the VIP receptor.

The VIP-neurotensin hybrid antagonist was also examined in another well characterized biological system to substantiate its pharmacological activity and to begin assessing the generality of these effects. The new molecule was also tested in cell cultures derived from the central nervous system (Evans et al. (1984) J. Neurochem. 43:131; Brenneman et al. (1987) J. Cell Biol. 104:1603). The VIP-neurotensin hybrid antagonist (10 µM) displaced 85-90% of VIP binding to glial cell cultures. This displacement curve was biphasic, indicating two binding sites, one with an $IC_{50}$ of 50 pM and another with an $IC_{50}$ of 0.1 µM. Moreover, under the same experimental conditions, unlabeled VIP (10 µM) produced 75% displacement.

Figure 3A:
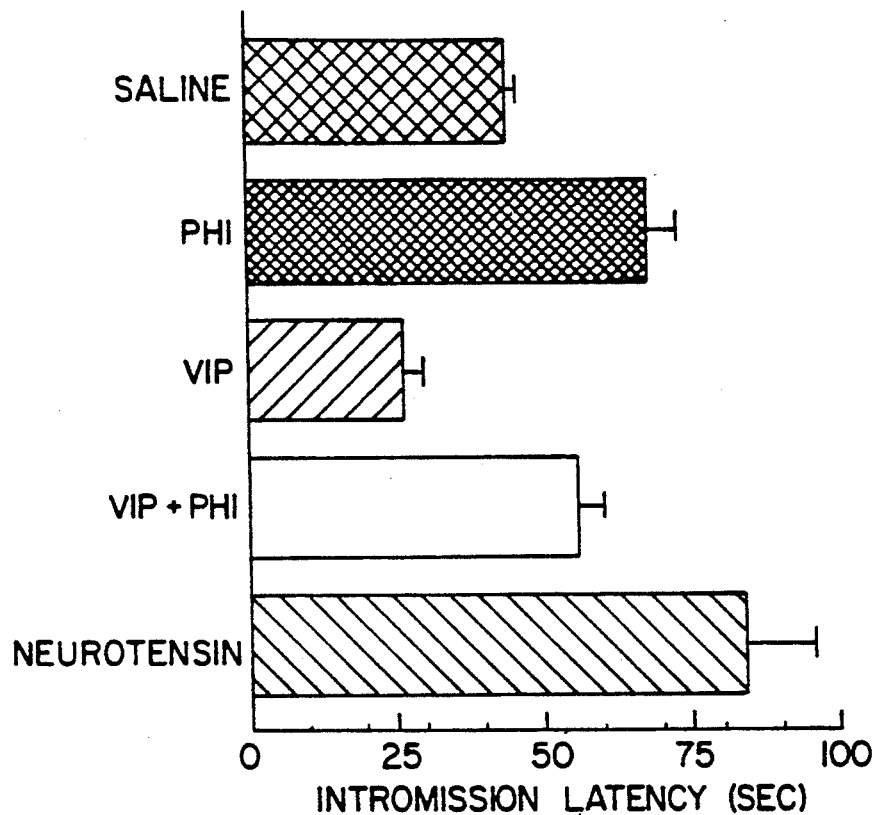
FIG. 3(A) The effects of PHI, VIP, VIP plus PHI, and neurotensin on the mean intromission latency. Experiments were performed as described in FIG. 1. VIP significantly decreased the mean intromission latency, which was prevented by PHI ($P<0.001$).
Figure 3B:
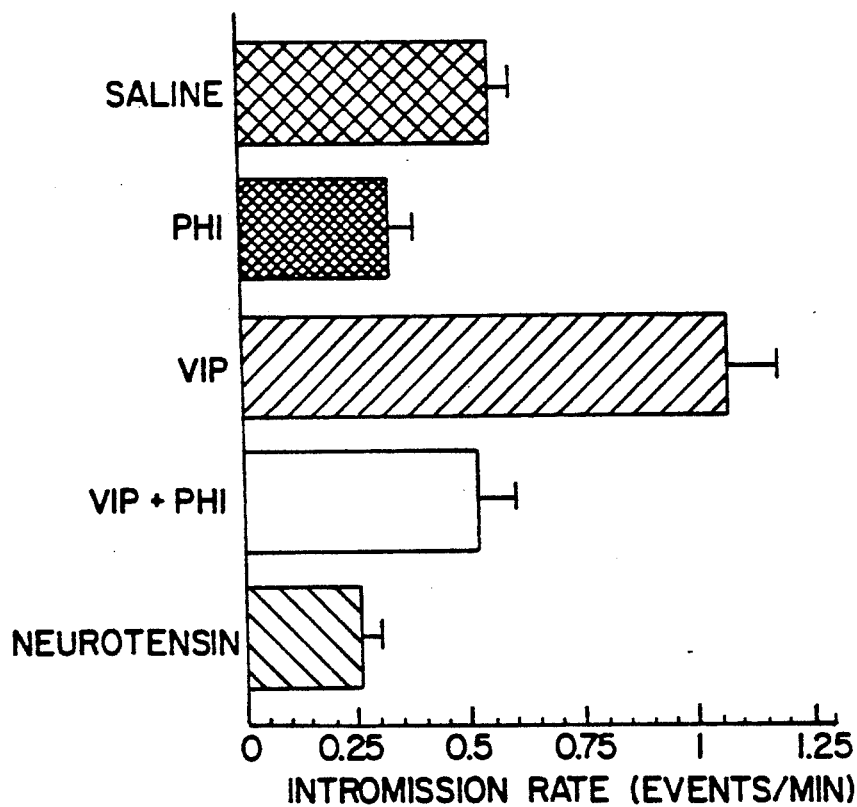
FIG. 3(B) The mean rate of intromission (copulatory events per min), which was measured over a 15-min test period. Analysis of variance indicated again that VIP injection significantly improved sexual function ($P<0.001$) as measured by intromission rates. Injection of PHI or neurotensin caused a decrease in sexual performances ($P<0.001$ and $P<0.003$, respectively, compared to the saline control).

As controls for specificity, peptides were investigated that exhibit structural similarity to VIP (Said and Mutt (1988) Ann. N.Y. Acad. Sci. 527:1; Gozes (1987) In: Brain peptides update. Wiley and Sons, New York, Vol. 1:141). While glucagon did not have any effect, peptide histidine isoleucine amide (PHI), which is cosynthesized with VIP on the same protein precursor (Gozes (1987) In: Brain peptides update. Wiley and Sons, New York, Vol. 1:141; Nishizawa et al. (1988) FEBS Lett. 183:55), apparently inhibited rat sexual behavior and VIP-induced rat sexual behavior (FIG. 3). Accordingly, the measured average latency to intromissions and rate of copulatory events in the presence of either PHI by itself or VIP plus PHI in equimolar concentrations were similar and 2-fold different from the values obtained with VIP by itself (FIG. 3). The same was found for the latency to the first intromission. Only one of nine animals ejaculated in the presence of PHI, which is similar to the saline control group. In cell culture, PHI has been shown to produce significant neuronal cell death, which can be antagonized by VIP (Brenneman and Foster (1987) Peptides 8:687).

EXAMPLE 3

Potency of VIP-Antagonist Using Lung Cancer Cells

The binding properties and the adenylate cyclase activity of the VIP receptor in NSCLC cell lines were investigated. NSCLC cells were cultured in RPMI-1640 containing 10% heat inactivated fetal bovine serum (Carney et al. (1985) Cancer Res. 45:2913-2923). When a monolayer formed, the adherent cells were washed with PBS and treated with trypsin/EDTA. The cells were pelleted and resuspended in serum supplemented medium and incubated at 37° C. in 5% $CO_2$/95% air. Routinely the cells were passed 1/1 weekly and experiments were conducted when the cells were in exponential growth phase.

Cells were rinsed twice in PBS. Membranes were prepared from EPLC-65H by lysing cells in 20 mM Tris.HCl (pH7.5), 1 mg/ml bacitracin, 1 mM PMSF and 0.25M sucrose. The cells were sonicated (15 sec, 120 W) and the membranes centrifuged at 500×g for 5 min in a Beckman J-21 B centrifuge at 4° C. The supernatant was saved and the pellet resuspended, homogenized and centrifuged. The supernatants were combined and centrifuged at 50,000×g for 30 min. The pellet, which contains plasma membranes, was resuspended and 50 µg of membrane protein and $2\times10^5$ cpm of $^{125}$I-VIP (2200 Ci/mmol) was added to each assay tube in a total volume of 100 µl; the buffer was 50 mM Tris.maleate, 2 mM $MgCl_2$, 2% BSA, 500 KIU/ml trasylol and 0.2 mg/ml bacitracin. The samples were incubated at 37° C. for 60 min. To terminate the reaction, the incubation solution was centrifuged for 3 min in a microfuge B. The supernatant, which contained free peptide was removed and the top of the pellet rinsed three times with cold assay buffer. The pellet, which contained bound $^{125}$I-VIP was counted in a gamma counter.

$^{125}$I was purchased from NEN. VIP was iodinated using the chloramine T procedure (Christophe et al. (1976) J. Biol. Chem. 251:4629-4634). $^{125}$I-VIP was purified using gel filtration techniques. VIP peptides were purchased from Peninsula Laboratories Inc. (San Carlos, Calif.).

The cAMP assays were performed by radioimmunoassay. 5M2 cells were exposed to stimuli in SIT medium (RPMI-1640 containing $10^{-8}$M $Se_2O_3$, 1 µg/ml insulin and $3\times10^{-8}$M transferrin) containing 100 mM isobutyl-methyl-xanthine. After 5 min, the reaction was quenched by adding an equal volume of ice cold ethanol. The samples were vortexed and an aliquot of supernatant removed and added to 100 µl of 50 mM sodium acetate (pH 6.2). The sample (25 µl) was acetylated at 4° C. by adding 10 µl of triethylamine followed by 5 µl of acetic anhydride. Then 200 µl of goat anti-cyclic AMP antibody was added followed by 8,000 cpm of $^{125}$I-2-succinyl (tyrosine methyl ester)-cyclic AMP (NEN). After incubation for 16 hr at 4° C., 1 ml of charcoal suspension (2 mg/ml Norit-A charcoal in 100 mM phosphate buffer, pH 6.3, which contains 0.25% BSA) was added, the tubes vortexed and centrifuged at 1,500×g for 10 min. An aliquot (1 ml) of supernatant, which contains radiolabeled antigen-antibody complex, was counted in a gamma counter.

Figure 4:
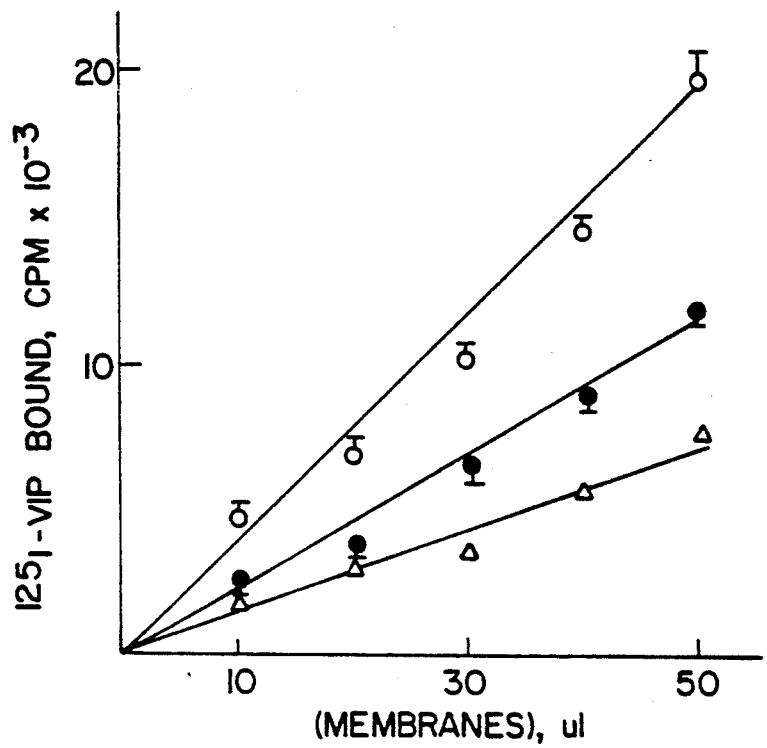
FIG. 4. Binding as a function of membrane concentration. The mean amount$\pm$S.E. of total (○) and non-specific binding (●) was determined as a function of EPLC-65H membrane concentration. The difference between the two represents specific binding ($\Delta$).

Initial binding studies indicated that $^{125}$I-VIP binding sites were uniformly distributed on NSCLC cells. Membranes from adenocarcinoma ADLC-5M2 and NCI-H23, large cell carcinoma NCI-H157 and H-460 and squamous cell carcinoma NCI-H520 and EPLC-65H bound $^{125}$I-VIP with high affinity. Because membranes from EPLC-65H bound $^{125}$I-VIP best it was used in subsequent binding experiments. Total and nonspecific binding of radiolabeled VIP was a linear function of membrane concentration (FIG. 4). The difference between the two represents specific binding and the ratio of specific/nonspecific binding was approximately 1/1. Routinely, 50 µl of membranes (50 µg protein) were used in binding experiments.

Figure 5:
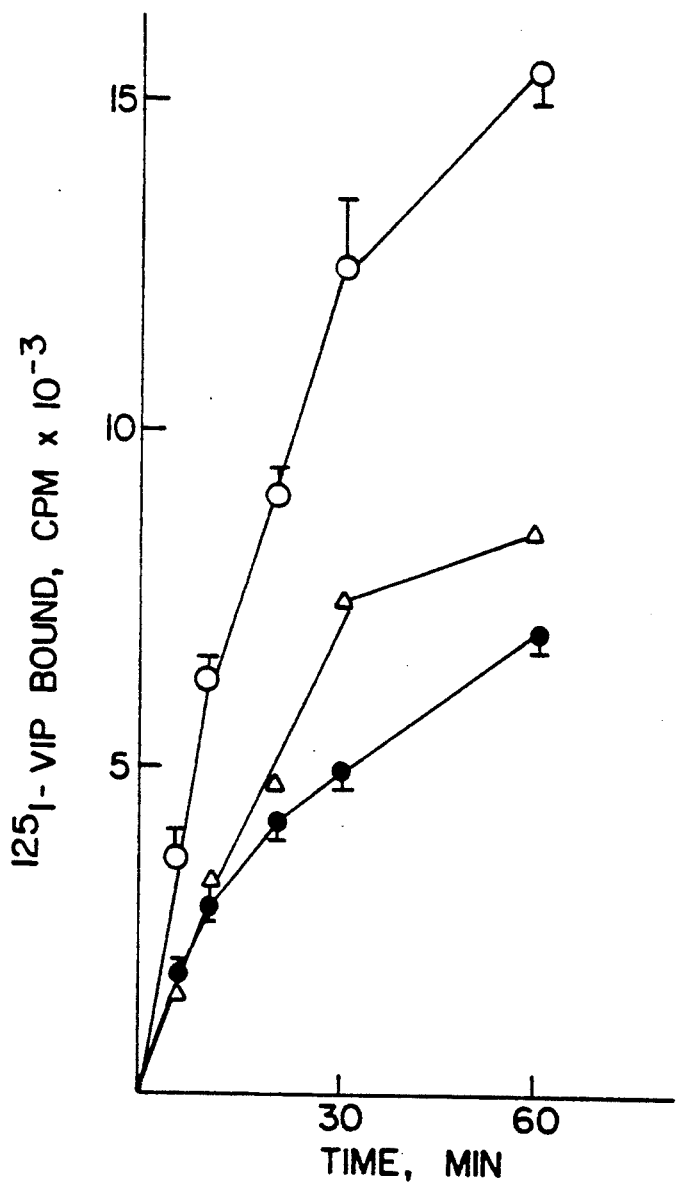
FIG. 5. Association kinetics. The amount of $^{125}$I-VIP bound to EPLC-65H membranes was determined as a function of time in the absence (○) and presence (●) of 1 $\mu$M unlabeled VIP. The difference b the two represents specific binding ($\Delta$). The mean value$\pm$S.D. of two determinations is indicated.

The kinetics of binding was investigated. FIG. 5 shows the association of $^{125}$I-VIP to EPLC-65H membranes. Total binding rapidly increased during the first 30 min then slowly increased. In contrast, nonspecific binding moderately increased in the first 10 min, then slowly increased. Specific binding was half maximal after 20 min and maximal after 60 min. The ratio of specific to nonspecific binding was approximately 1/1.

Figure 6:
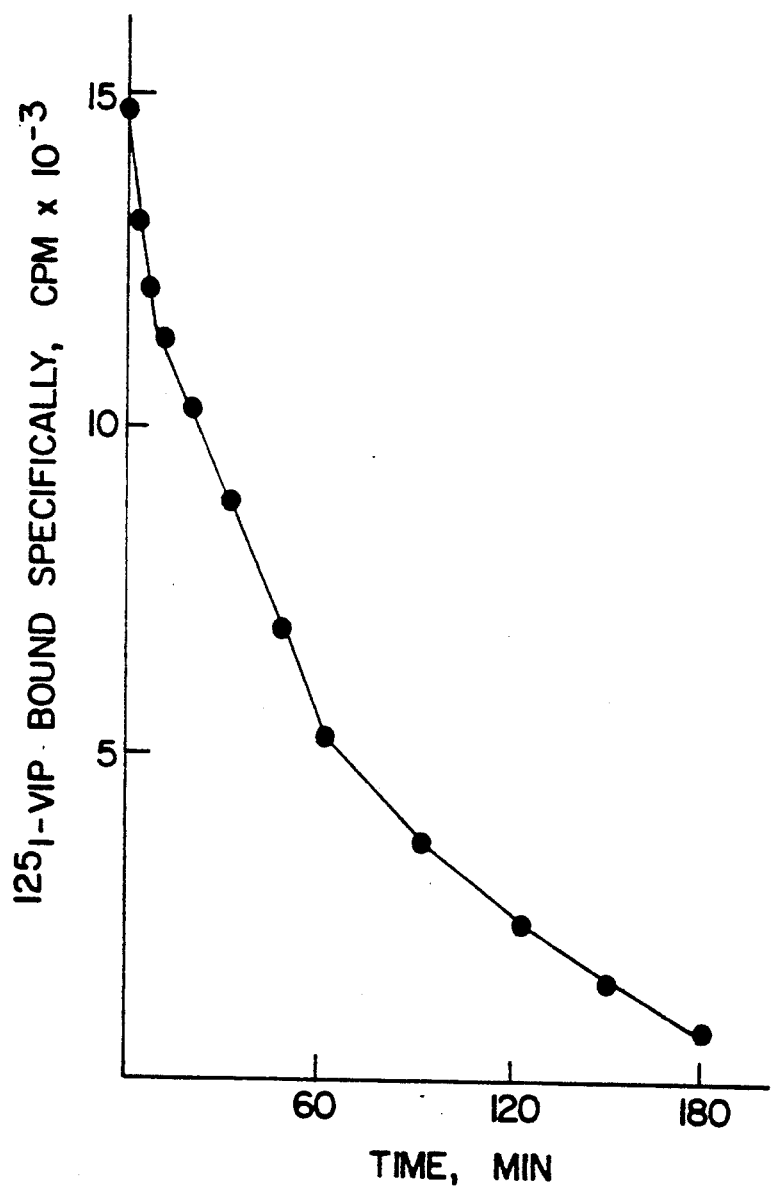
FIG. 6. Dissociation kinetics. $^{125}$I-VIP was incubated with EPLC-65H membranes for 30 min. and the amount of specifically bound $^{125}$I-VIP determined as a function of time after the addition of 1 $\mu$M unlabeled VIP.

Specific $^{125}$I-VIP binding was reversible (FIG. 6). Half of the specific binding was reversed 40 min after the addition of 1 μM unlabeled VIP and almost all specific binding was reversed after 3 hr.

Figure 7A:
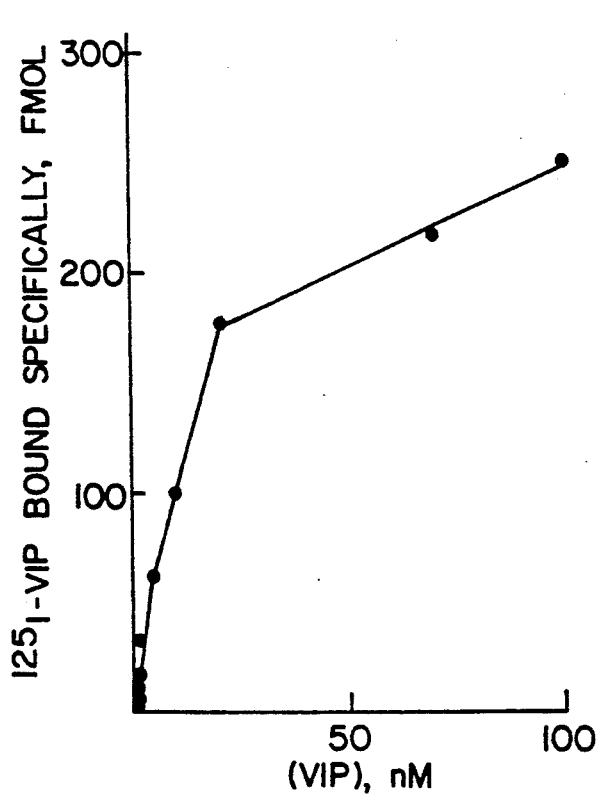
FIG. 7A (Left) The amount of $^{125}$I-VIP bound specifically was determined as a function of radiolabeled VIP concentration.
Figure 7B:
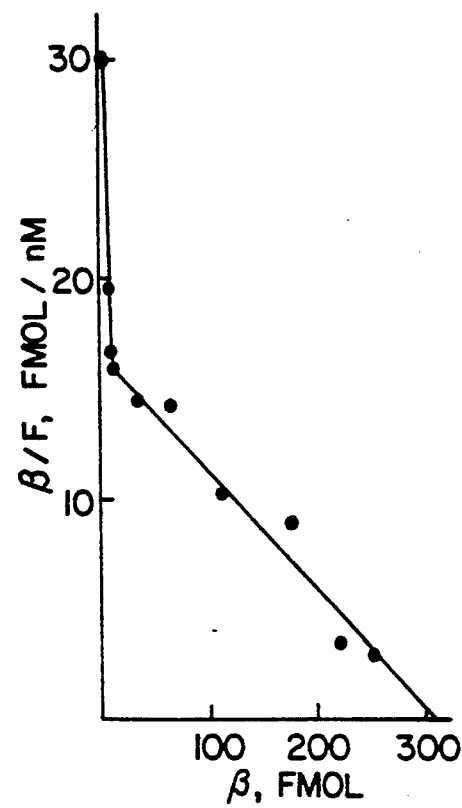
FIG. 7B (Right) A Scatchard replot of the specific binding data as shown.

The amount of radiolabeled VIP bound was concentration dependent. FIG. 7 shows that specific $^{125}$I-VIP binding rapidly increased at low VIP concentrations e.g. 1 nM, however, specific binding slowly increased at high VIP concentrations e.g. 50 nM. A Scatchard replot of the specific binding data was biphasic and consisted of high (Kd=0.7 nM) and low affinity (Kd=20 nM) sites. The density of low and high affinity sites was 400 and 6200 fmol/μg protein respectively.

Figure 8:
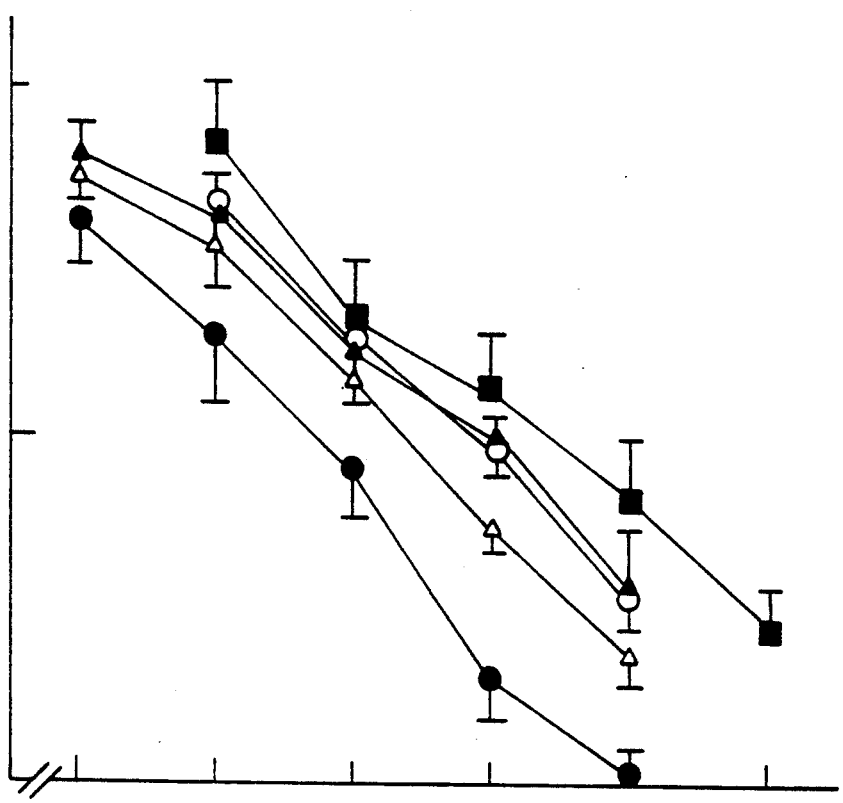
FIG. 8. Specificity of binding. The amount of $^{125}$I-VIP bound specifically was determined as a function of unlabeled VIP (●), PHI (○), GHRH ($\Delta$), helodermin (▲) and secretin (□) concentration. The mean value$\pm$S.E. of 3 determinations each repeated in duplicate is shown.

The specificity of $^{125}$I-VIP binding was investigated. Little specific $^{125}$I-VIP binding was inhibited by low peptide concentrations e.q. 0.1 nM whereas most specific $^{125}$I-VIP binding was inhibited by high peptide concentrations e.g. 1 μM (FIG. 8). The IC$_{50}$ for GHRH was 20 nM. In contrast, VIP was more potent with an IC$_{50}$ value of 10 nM. PHI, helodermin, and secretin were less potent with IC$_{50}$ values of 0.08, 0.1, and 0.3 μM, respectively.

Figure 9:
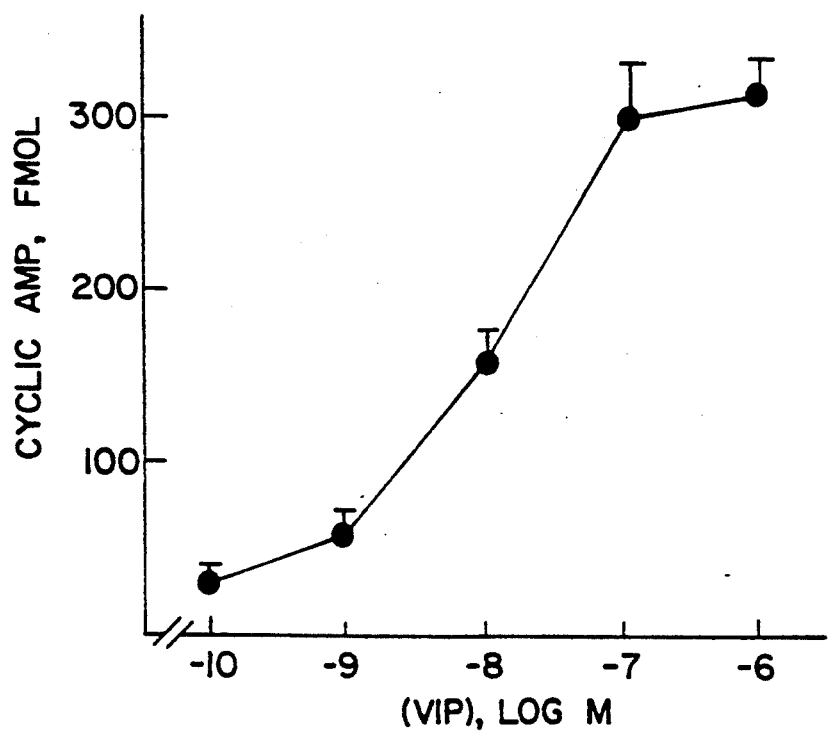
FIG. 9. VIP elevates cAMP. The amount of cAMP produced as a function of VIP concentration was determined. The mean value$\pm$S.E. of 4 determinations is indicated.

The ability of VIP to stimulate adenylate cyclase activity was investigated. FIG. 9 shows that VIP increased the cAMP levels in a dose dependent manner and the ED$_{50}$ was 10 nM.

In summary, because VIP binds with high affinity to NSCLC cells and stimulates adenylate cyclase activity, VIP receptors may be biologically active in this tumor. Therefore, a determination of whether the VIP-neurotensin hybrid antagonist could be used to inhibit growth of NSCLC cells was made.

The ability of VIP and VIP-neurotensin hybrid antagonist peptides to inhibit specific $^{125}$I-VIP binding to EPLC-65H membranes was determined three times and the mean value was determined. VIP and VIP-neurotensin hybrid antagonist both had an IC$_{50}$ value of 10 nM. Similar data was obtained using NCI-H838 and NCI-H522 membranes. This data indicates that this VIP antagonist inhibited binding to NSCLC VIP receptors with high affinity. Thus the VIP-neurotensin hybrid antagonist bound as tightly to the VIP receptor as did VIP.

In order to test whether the VIP-neurotensin hybrid antagonist inhibited the growth of NSCLC, single viable cells (10$^4$) were plated in soft agar in the absence and presence of 1 μM VIP-neurotensin hybrid antagonist. After 2 weeks, colonies were stained with a vital dye and live colonies (>50 nm) counted. The colony fraction (colonies in the presence of the VIP-neurotensin hybrid antagonist relative to the number of basal colonies) was calculated. Cell lines NCI-H522, NCI-H838, and NCI-H1246 had colony fractions of 0.45±0.16, 0.76±0.04, and 1.47±0.30, respectively. The VIP-neurotensin hybrid antagonist inhibited colony formation of cell lines NCI-H522 and NCI-H838 but not NCI-H1246.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( D ) TOPOLOGY: linear ( x i ) SEQUENCE DESCRIPTION: SEQ ID NO:1:

```
Lys  Pro  Arg  Arg  Pro  Tyr
1                 5
```

( 2 ) INFORMATION FOR SEQ ID NO:2:

( i ) SEQUENCE CHARACTERISTICS:
      ( A ) LENGTH: 28 amino acids
      ( B ) TYPE: amino acid
      ( D ) TOPOLOGY: linear ( x i ) SEQUENCE DESCRIPTION: SEQ ID NO:2:

```
Lys  Pro  Arg  Arg  Pro  Tyr  Thr  Asp  Asn  Tyr  Thr  Arg  Leu  Arg  Lys  Gln
1                 5                           10                          15

Met  Ala  Val  Lys  Lys  Tyr  Leu  Asn  Ser  Ile  Leu  Asn
                 20                          25
```

( 2 ) INFORMATION FOR SEQ ID NO:3:

( i ) SEQUENCE CHARACTERISTICS:
      ( A ) LENGTH: 8 amino acids (B) TYPE: amino acid
(D) TOPOLOGY: linear (xi) SEQUENCE DESCRIPTION: SEQ ID NO:3:

Leu Met Tyr Pro Thr Tyr Leu Lys
1               5

Leu—Asn—Ser—Ile—Leu—Asn—NH$_2$.

What is claimed is:

1. A vasoactive intestinal polypeptide (VIP) antagonist, said antagonist having the following amino acid sequence (Seq. I.D. No. 2):

Lys—Pro—Arg—Arg—Pro—Tyr—Thr—Asp—Asn—Tyr—Thr—

Arg—Leu—Arg—Lys—Gln—Met—Ala—Val—Lys—Lys—Tyr—

2. A method of antagonizing VIP activity in a mammal comprising administering an effective amount of the VIP antagonist of claim 1 to said mammal.

3. A method of inhibiting the effect of VIP on the sexual behavior of a mammal comprising administering an effective amount of the VIP antagonist of claim 1 to said mammal.

* * * * *